US006973672B2

(12) United States Patent  (10) Patent No.: US 6,973,672 B2
Huh  (45) Date of Patent: Dec. 13, 2005

(54) WELDING HELMET REMOVABLE CARTRIDGE

(75) Inventor: Moon Young Huh, Seoul (KR)

(73) Assignee: Otos Tech Co., Ltd., Seoul (KR)

( * ) Notice: Subject to any disclaimer, the term of this patent is extended or adjusted under 35 U.S.C. 154(b) by 37 days.

(21) Appl. No.: 10/804,662

(22) Filed: Mar. 19, 2004

(65) Prior Publication Data

US 2004/0210976 A1 Oct. 28, 2004

(30) Foreign Application Priority Data

Mar. 20, 2003 (KR) ........................ 10-2003-0017433

(51) Int. Cl.⁷ .............................................. A61F 9/06
(52) U.S. Cl. ................................................... 2/8
(58) Field of Search ........................... 2/8, 441, 431, 2/432, 453, 427, 429; 219/147; 349/58; 359/892

(56) References Cited

U.S. PATENT DOCUMENTS

| | | | | |
|---|---|---|---|---|
| 1,378,255 A | * | 5/1921 | Malcom | 2/8 |
| 1,777,701 A | * | 10/1930 | Ramstein | 2/453 |
| 1,833,257 A | * | 11/1931 | Norton | 2/8 |
| 1,887,654 A | * | 11/1932 | Mahon | 126/200 |
| 2,050,890 A | * | 8/1936 | Lynn | 2/453 |
| 2,270,028 A | * | 1/1942 | Anderson | 2/8 |
| 2,411,224 A | * | 11/1946 | O'Reilly | 2/8 |
| 2,726,395 A | * | 12/1955 | Anderson | 2/8 |
| 3,251,065 A | * | 5/1966 | Caldwell | 2/8 |
| 3,311,922 A | * | 4/1967 | Bezzerides | 2/8 |
| 4,648,394 A | * | 3/1987 | Wise | 128/201.24 |
| 5,533,206 A | * | 7/1996 | Petrie et al. | 2/8 |
| 5,548,448 A | * | 8/1996 | Wagner | 359/802 |
| 6,185,739 B1 | * | 2/2001 | Verkic et al. | 2/8 |
| 6,357,053 B1 | * | 3/2002 | Wang-Lee | 2/431 |

FOREIGN PATENT DOCUMENTS

| | | | | | |
|---|---|---|---|---|---|
| GB | 2139373 A | * | 11/1984 | | F16P 1/06 |
| GB | 2225646 A | * | 6/1990 | | A61F 9/06 |

* cited by examiner

Primary Examiner—Rodney M. Lindsey
(74) Attorney, Agent, or Firm—Jordan and Hamburg LLP

(57) ABSTRACT

A welding helmet includes a helmet body for covering the face of an operator, an opening in a front surface of the helmet body, a cartridge for protecting the eyes of the operator from light generated during a welding operation, and structure including hooks projected from an upper side of the opening in the helmet body, pressing projections projected from both sides of the opening in the helmet body, hooking projections projected from an upper side of the cartridge to engage with the hooks, and fitting projections from both sides of the cartridge to fit to the pressing projections, the aforementioned structure removably engaging the cartridge to the helmet body. Fumes generated upon welding or cutting are prevented from directly flowing into the helmet body and injurious light generated upon welding is blocked. The cartridge can be readily removed for repair or replacement.

5 Claims, 5 Drawing Sheets

WELDING HELMET REMOVABLE CARTRIDGE

BACKGROUND OF THE INVENTION

1. Field of the Invention

The present invention relates to a welding helmet with a removable cartridge, and more particularly to a welding helmet for preventing fumes generated upon welding or cutting from directly flowing into the helmet as well as shutting off light generated upon welding or cutting.

2. Description of the Related Art

As well known to those skilled in the art, a helmet for welding has been used to protect the eyes of a worker in case of welding or cutting. A glare protector (hereinafter, referred as "cartridge") is fixed to the helmet for protecting the eyes of the worker from intense injurious light generated during welding or cutting. The cartridge shuts off light in the wavelength range of 780 nm (IB) to 365 nm (UV) and controls transmitted quantity of the visible ray to allow the worker to ascertain welding position without glare.

U.S. Pat. No. 5,533,206 discloses a welding helmet including an LCD (Liquid Crystal Display) lens positioned directly in front of a wearer for serving as an actual view window, a solar cell functioning as an energy input by absorbing light, an EQC (Electronic Quick Change) cartridge having photo sensor cells detecting sparks and other intense light and acting as an input to a circuit that automatically adjusts the LCD lens to a variable opaque condition, and a cartridge housing positioned within the helmet for securing the EQC cartridge within the helmet.

Further, U.S. Pat. No. 6,070,264 discloses a welding helmet including a shutter mounted so that a helmet wearer may view welding operation, an electronic control connected for controlling a light transmission shade of the shutter, a photo sensor for detecting the bright light emanating from the welding operation, and electronic circuitry for changing the shade of the shutter to darken it in responsive to the photo sensor.

The above stated welding helmets are provided with a cartridge for automatically driving the shade of the LCD lens or the shutter to darken it in order to detect intense light generated during welding and protect the eyes of the worker from the intense light. However, such a cartridge has problems that it is not removably mounted to the welding helmet or not easily mounted to and removed from the welding helmet.

Further, the prior helmet with a removable cartridge has a problem that, since the engagement between the helmet body and the cartridge is not made sufficiently, fumes generated during welding or cutting directly flow into a gap between the helmet body and the cartridge, thereby mortally injuring a worker's health.

SUMMARY OF THE INVENTION

Therefore, the present invention has been made in view of the above problems, and it is an object of the present invention to provide a welding helmet with a removable cartridge for preventing fumes generated during operation from directly flowing into the helmet as well as shutting off light generated upon welding or cutting.

In accordance with the present invention, the above objects can be accomplished by the provision of a welding helmet comprising a helmet body for covering the face of an operator, an opening formed in a front surface of the helmet body, a cartridge fitted to the opening for protecting the eyes of the operator from light generated during a welding operation, and means for removably engaging the cartridge to the helmet body and including hooks projected from an upper side of the opening in the helmet body, pressing projections projected from both sides of the opening in the helmet body, respectively, hooking projections projected from an upper side of the cartridge to engage with the hooks, and fitting projections from both sides of the cartridge to fit to the pressing projections, respectively.

Preferably, the pressing projections may be made of an elastic material so that the pressing projections are widened toward both sides thereof and returned to their original positions after fitting to the fitting projections.

Further, preferably, the pressing projections may be formed with supporting jaws pressing the fitting projections when the pressing projections are returned to their original positions.

Further, preferably, the helmet may be provided at the inside thereof with a fence projected at a predetermined height along a margin of the opening. The cartridge may be formed with a fence fitting groove connected along a margin of the cartridge to fit to the fence.

Further, preferably, a protecting cover made of a transparent material for protecting the cartridge may be interposed between the helmet body and the cartridge.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
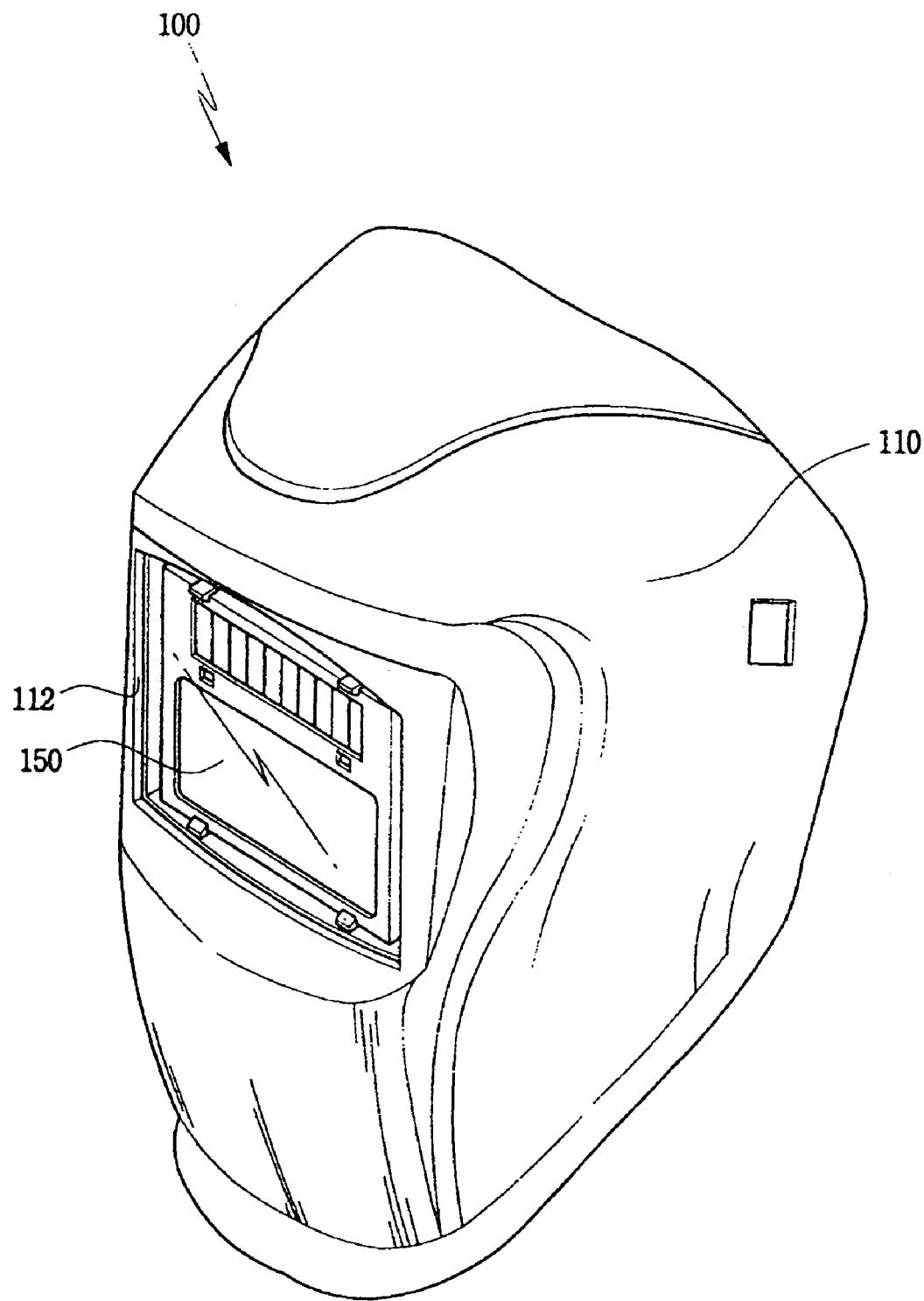
FIG. 1 is a perspective view of a welding helmet according to the present invention.
Figure 2:
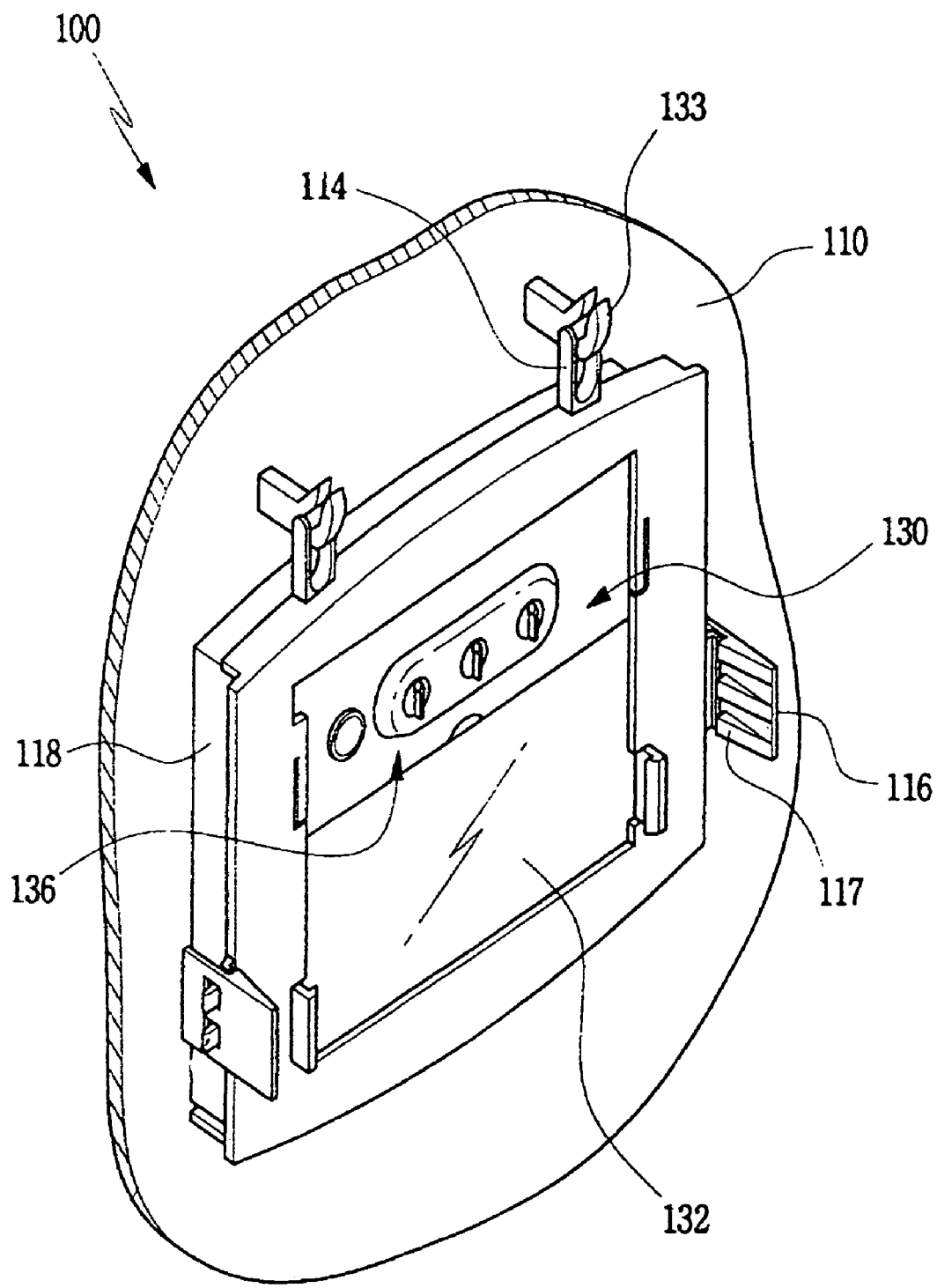
FIG. 2 is a perspective view showing the inside of the welding helmet shown in FIG. 1.
Figure 3:
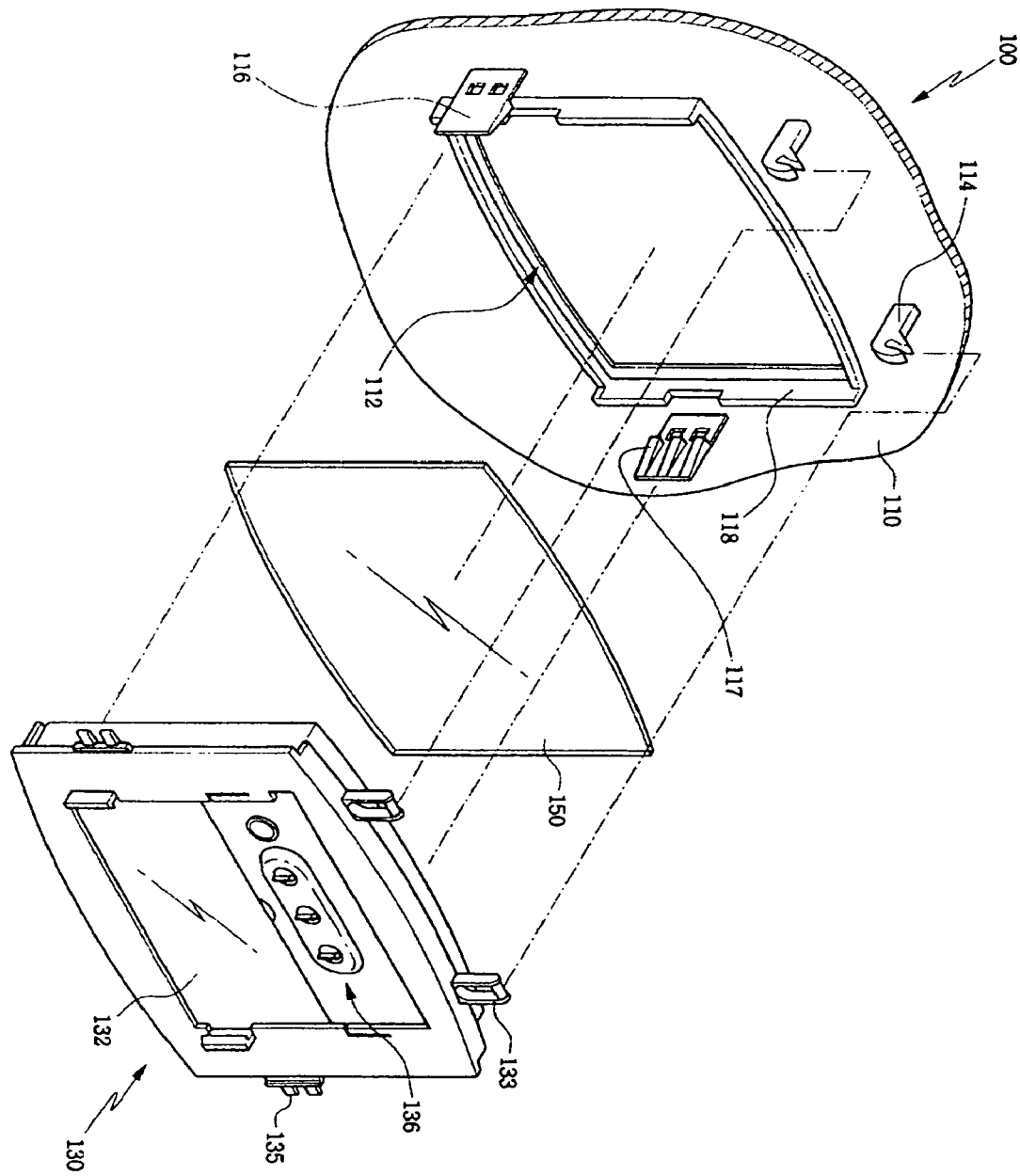
FIG. 3 is an exploded perspective view of the welding helmet shown in FIG. 2.
Figure 4:
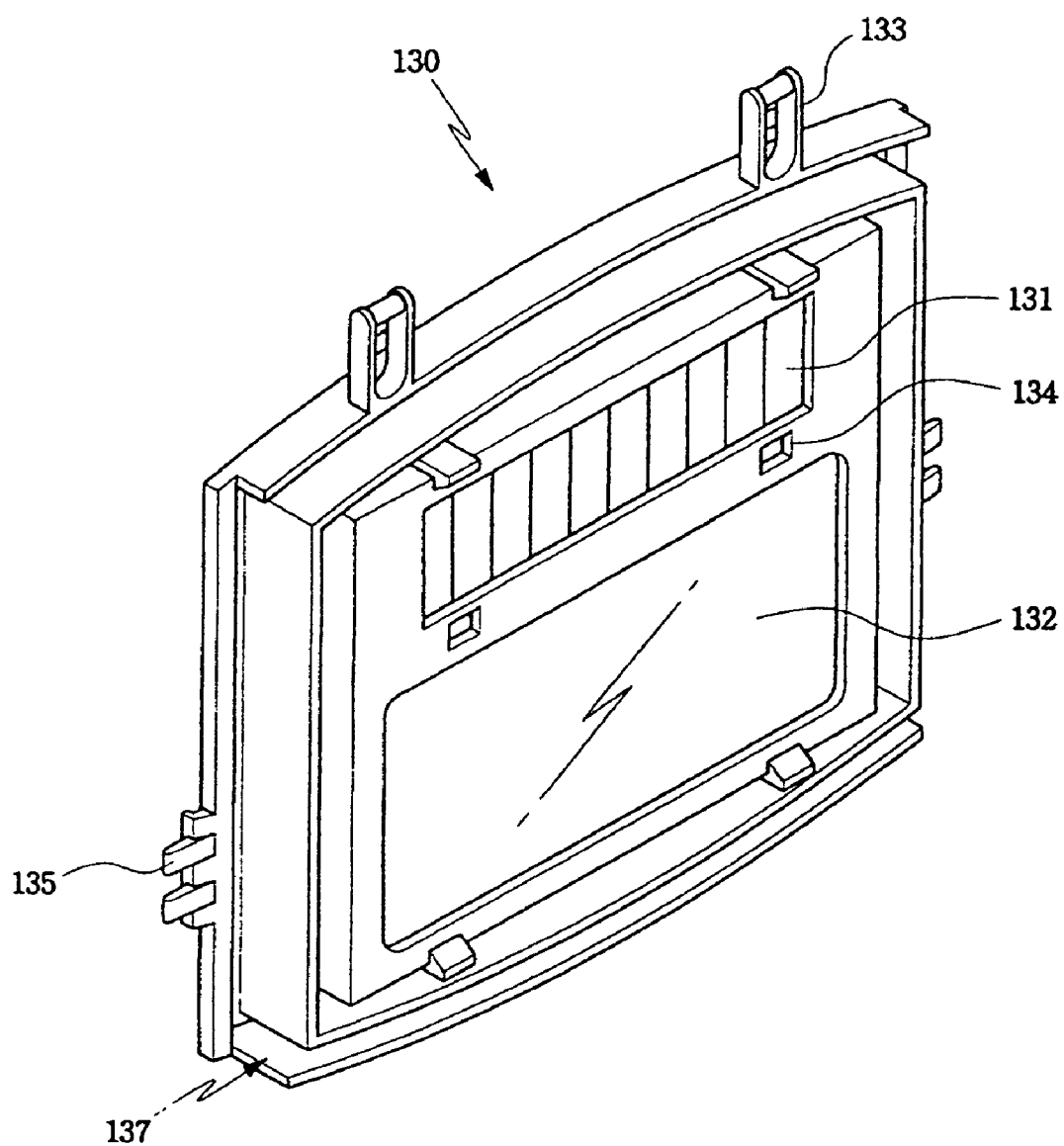
FIG. 4 is a perspective view of a cartridge of the welding helmet according the present invention.
Figure 5:
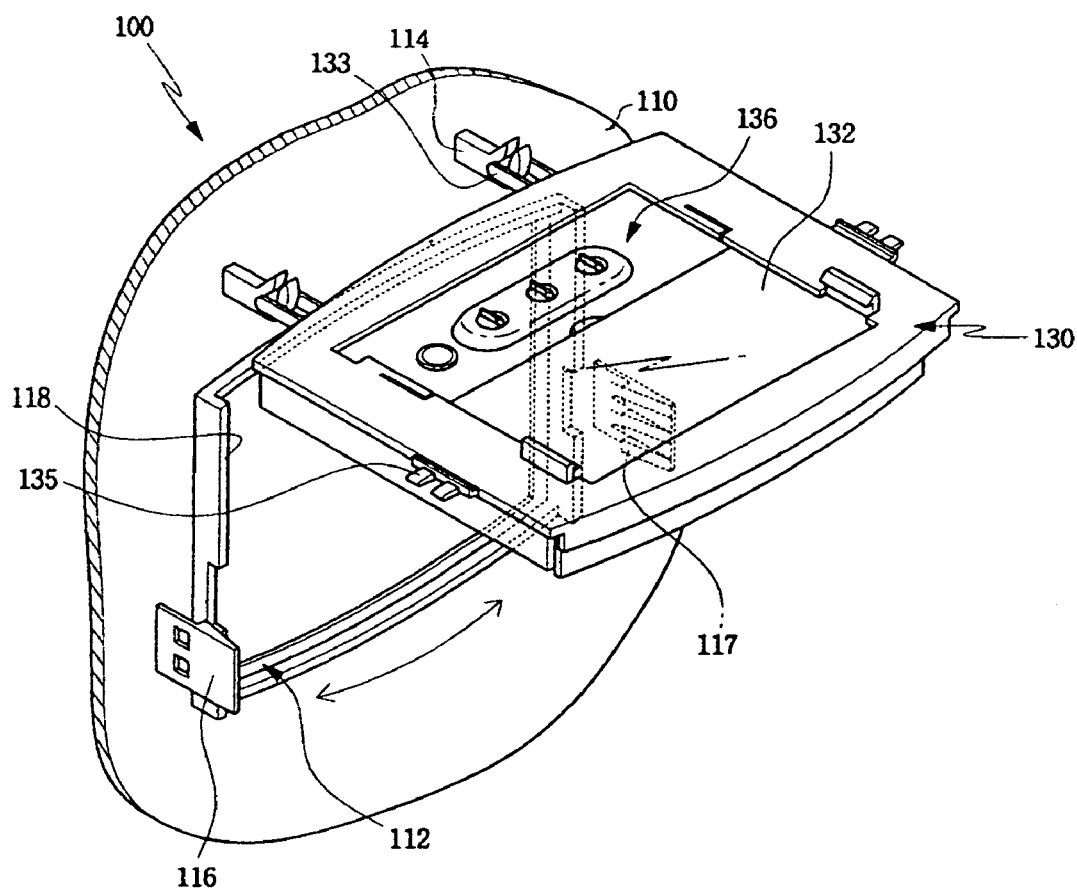
FIG. 5 is a perspective view showing the status of fitting the cartridge to the welding helmet of the present invention.

FIG. 1 is a perspective view showing an embodiment of a welding helmet with a removable cartridge according to the present invention, and FIG. 2 is a perspective view showing the inside of the welding helmet according to the present invention.

As shown in FIGS. 1 and 2, a welding helmet 100 according to the present invention includes a helmet body 110 formed to cover the face of a worker (not shown), a cartridge 130 mounted within the helmet body 110, and a protecting cover 150 interposed between the helmet body 110 and the cartridge 130.

Here, the helmet body 110 may be made of a lightweight material, such as plastic. A front side of the helmet body 110 is formed with an opening 112 having a rectangular shape. The cartridge 130 is removably mounted to the opening 112 of the helmet body 100.

Further, a structure for removably mounting the cartridge 130 is provided on the margin of the opening 112 in the inside of the helmet body 110 and at the site of the cartridge 130 corresponding to the margin of the opening 112.

More specifically, the inside of the helmet body 110 is formed with a fence 118 having a flat-plate shape projected at a predetermined height along the margin of the opening 112.

Further, hooks 114 for hanging the cartridge 130 are projected on the upper side of the fence 118. Pressing projections 116 are formed on the both sides of the fence 118 to fit to the cartridge 130 and press the cartridge 130 after fitting the cartridge 130, respectively. Here, preferably, the pressing projections 116 may be made of elastic material so that the pressing projections 116 are widened toward both sides and returned to their original positions after fitting. Further, preferably, the pressing projection 116 may be formed with a guide rail 117 projected at a predetermined height to press the cartridge 130 when returning to their original positions after fitting.

Here, a portion of the fence 118 facing the pressing projection 116 is formed with a cut-off portion. The cut-off portions of the fence 118 serve to receive fitting projections 135 of the cartridge 130 to be described hereinafter.

Meanwhile, the cartridge 130 has the shape of a rectangular panel. The cartridge 130 consists of a light detector 134 detecting injurious light generated upon welding or cutting, a charging solar battery 13 supplying an electric source to drive the cartridge 130, an LCD panel driving shade to darken according to the detection of the light detector 134 to protect the worker form the injurious light and an LCD driver (not shown) driving the LCD panel 132, a controller (not shown) outputting driving signal to the LCD driver if light is detected by the light detector 134, and a manual operating section 136 for enabling manual operation. The cartridge 130 serves to sense intense light generated during welding and drive the shade of the LDC panel 132 to go darker in order to protect the eyes of the worker. Further, as described above, the cartridge 130 is removably mounted within the opening 112 of the helmet body 110.

The cartridge is formed with hooking projections 133, the fitting projections 135 and a fence fitting groove 137 corresponding to the hooks 112, the pressing projections 116 and the fence 118 in the helmet body 110, respectively.

Specifically, one side of the cartridge 130 facing the fence 118 is formed with the fence fitting groove 137 connected along the margin of the cartridge 130. The upper side of the fence fitting groove 137 is formed with the hooking projections 133 having a loop shape to hang on the hooks 114. Both sides of the fence fitting groove 137 are formed with the fitting projections 135 projected at a predetermined height to fit to the pressing projections 116, respectively.

Meanwhile, the protecting cover 150 may be made of a transparent resin and has a size for fitting in the opening 112. The protecting cover 150 is interposed between the helmet body 110 and the cartridge 130 and serves to prevent a spark generated upon welding or cutting from flying up directly to the cartridge 130. Further, the protecting cover 150 is pressed between the helmet body 110 and the cartridge 130 and serves to prevent fumes generated upon welding or cutting from flowing directly into the helmet body 110.

The operation and effects of the welding helmet 100 with the removable cartridge according to the present invention will be given herein below.

Firstly, the worker fits the protecting cover 150 in the opening 112 of the helmet body 110 and then fits the cartridge 130 on the rear side of the protecting cover 150. As a result, assembly of the welding helmet 100 according to the invention is finished.

At this time, in order to engage the cartridge 130 with the welding helmet 100, after engaging the cartridge 130 to the protecting cover 150, the worker fits and hangs the hooking projections 133 of the cartridge 130 on the hooks 114 of the helmet body 110 and then fits the cartridge 130 to the helmet body 110.

The cartridge 130 is fitted to the helmet body 110 by rotating about the hooking projections 133 hung on the hooks 114. The cartridge 130 is fitted to the helmet body 110 until the fitting projections 135 of the cartridge 130 pushing the pressing projections 116 to outside thereof, respectively, and then are placed beneath the supporting jaws 117 of the pressing projections 116. Then, the pressing projections 116 of the helmet body 110 are returned to their original position, as before the cartridge 130 is fitted, due to their elasticity. As a result, the pressing projections 116 press strongly against the rear part of the cartridge 130 through the supporting jaws 117 of the pressing projections 116.

At this time, the fence 118 of the cartridge 130 is fitted into the fence fitting groove 137 with the cartridge 130 fitting to the helmet body 110.

Then, after assembly of the welding helmet 100, the worker conducts an operation, such as welding or cutting while covering his/her face with the welding helmet 100.

Upon welding or cutting, intense light is generated at welding or cutting site.

Thus, the light detector 134 of the cartridge 130 mounted in the welding helmet 100 detects the intense light and transmits a detected light signal to the controller. The controller receives the light signal and outputs a driving signal for driving the LCD Panel 132 to the LCD driver.

Then, an LCD driver receives the LCD driving signal from the controller and controls light transmission of the LCD panel 132. AS a result, the LCD panel 132 is driven to protect light generated upon welding or cutting, and the shade of the LCD panel 132 is changed to darken it. Thus, the eyes of the worker are protected.

Meanwhile, fumes having a bad influence on the human body as well as intense injurious light are generated from the welding or cutting portion.

In the prior art, the fumes have directly flowed into the helmet body through the engaging portions between the helmet body 110 and the cartridge 130. However, according to the welding helmet 100, the direct inflow of the fumes through the opening, as in the prior art, is prevented since the cartridge 130 and the helmet body 110 are accurately and strongly pressed and secured together by the fence 118 of the helmet body 110 and the fence fitting groove 137, and the pressing projections 116 of the helmet body 110 and the hooking projections 135 of the cartridge 130.

In case of repairing the cartridge 130 or exchanging a part of the cartridge 130, the worker pushes each pressing projection 116 of the helmet body 110 in the direction for widening to the outside thereof and removes the fitting projections 135 of the cartridge 130 from the pressing projection 116 of the helmet body 110. After removing the fitting projections 135, the cartridge 130 is easily separated from the helmet body 110 by removing the hooking projections 133 from the hooks 114 of the helmet body 110. Then, the worker takes the cartridge 130 separated from the helmet body 110 and then repairs the cartridge 130 or exchanges the part of the cartridge 130.

As apparent from the above description, according to the welding helmet 100 with the removable cartridge, since the cartridge 130 is mounted on the front of the helmet body 100, the eyes of the worker are protected from the light generated upon welding or cutting. Further, in case of requiring repair of the cartridge 130 and the exchange of the parts of the cartridge 130, the worker easily removes the cartridge 130 from the helmet body 110 using the removable structure.

Further, according to the welding helmet 100 of the present invention, when the cartridge 130 is fitted in the helmet body 110, the fence fitting groove 137 of the cartridge 130 is exactly fitted to the fence 118 of the helmet body 110. Further, the cartridge 130 is strongly pressed and secured to the helmet body 110 by the removable structure consisting of the hooks 114 and pressing projections 116 of the helmet body 110 and the hooking projections 133 and fitting projections 135 of the cartridge 130. Thus, fumes generated upon welding or cutting are fully prevented from inflowing into the helmet body 110 through the opening 112 of the helmet body 110.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A welding helmet comprising:
    a helmet body for covering the face of an operator;
    an opening formed in a front surface of the helmet body;
    a cartridge fitted to the opening for protecting the eyes of the operator from light generated during a welding operation; and
    means for removably engaging the cartridge to the helmet body, the means including hooks projected from an upper side of the opening in the helmet body, pressing projections projected from both sides of the opening in the helmet body, respectively, hooking projections projected from an upper side of the cartridge to engage with the hooks, and fitting projections from both sides of the cartridge to fit to the pressing projections, respectively.

2. The welding helmet as set forth in claim 1, wherein the pressing projections are made of an elastic material, the pressing projections being widened toward both sides thereof and returned to their original positions after fitting to the fitting projections.

3. The welding helmet as set forth in claim 2, wherein the pressing projections are formed with supporting jaws pressing the fitting projections when the pressing projections are returned to their original positions.

4. The welding helmet as set forth in any one of claims 1 to 3, wherein the helmet is provided at the inside thereof with a fence projected at a predetermined height along a margin of the opening, the cartridge being formed with a fence fitting groove connected along a margin of the cartridge to fit to the fence.

5. The welding helmet as set forth in claim 1, wherein a protecting cover made of transparent material for protecting the cartridge is interposed between the helmet body and the cartridge.

* * * * *